US011719613B2

(12) United States Patent
He et al.

(10) Patent No.: US 11,719,613 B2
(45) Date of Patent: Aug. 8, 2023

(54) METHOD AND DEVICE FOR QUANTIFYING VISCOELASTICITY OF A MEDIUM

(71) Applicant: WUXI HISKY MEDICAL TECHNOLOGIES CO., LTD., Wuxi (CN)

(72) Inventors: Qiong He, Wuxi (CN); Jinhua Shao, Wuxi (CN); Jin Sun, Wuxi (CN); Houli Duan, Wuxi (CN); Qiang Wang, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 567 days.

(21) Appl. No.: 16/746,698

(22) Filed: Jan. 17, 2020

(65) Prior Publication Data
US 2020/0150013 A1 May 14, 2020

Related U.S. Application Data

(63) Continuation of application No. PCT/CN2018/088405, filed on May 25, 2018.

(30) Foreign Application Priority Data

Jul. 21, 2017 (CN) .......................... 201710649552.9

(51) Int. Cl.
G01N 11/16 (2006.01)
A61B 8/08 (2006.01)
G06T 7/40 (2017.01)

(52) U.S. Cl.
CPC ............ *G01N 11/16* (2013.01); *A61B 8/0858* (2013.01); *A61B 8/485* (2013.01); *A61B 8/5207* (2013.01);
(Continued)

(58) Field of Classification Search
None
See application file for complete search history.

(56) References Cited

U.S. PATENT DOCUMENTS

2008/0022758 A1 1/2008 Cottais
2008/0249408 A1 10/2008 Palmeri
(Continued)

FOREIGN PATENT DOCUMENTS

CN 101034004 A 9/2007
CN 101431943 A 5/2009
(Continued)

OTHER PUBLICATIONS

The first Office Action of the parallel RU application.
(Continued)

Primary Examiner — Shahdeep Mohammed
(74) Attorney, Agent, or Firm — J.C. Patents

(57) ABSTRACT

A method for quantifying viscoelasticity of a medium includes: obtaining a position-time graph of vibration propagation after the medium is subjected to a vibration excitation, determining an angle with maximum signal energy in the position-time graph by using angle projection, where the angle with the maximum signal energy corresponds to a slope of the position-time graph and the slope of the position-time graph is the propagation velocity of the vibration in the medium. Since the propagation velocity of the vibration in the medium is related to the viscoelasticity of the medium, a viscoelasticity parameter of the medium can be quantitatively calculated after the slope of the position-time graph is obtained. The method does not need to select a feature point from the position-time graph to calculate the slope of the position-time graph, and can efficiently and accurately quantifies viscoelasticity of the medium.

5 Claims, 3 Drawing Sheets

(52) U.S. Cl.
CPC ........ *G06T 7/40* (2013.01); *G01N 2203/0094* (2013.01)

(56) References Cited

U.S. PATENT DOCUMENTS

| | | | |
|---|---|---|---|
| 2010/0081929 | A1 | 4/2010 | Suzuki |
| 2014/0296709 | A1 | 10/2014 | Fatemi |
| 2015/0024473 | A1 | 1/2015 | Wu |
| 2015/0141822 | A1 | 5/2015 | Miyauchi |
| 2016/0199034 | A1* | 7/2016 | Labyed ............... G01S 15/8977 600/438 |
| 2016/0220232 | A1 | 8/2016 | Takada et al. |
| 2016/0262706 | A1 | 9/2016 | Zhao |
| 2016/0274067 | A1 | 9/2016 | Walker et al. |
| 2017/0156700 | A1* | 6/2017 | Honjo ................... A61B 8/485 |
| 2020/0150013 | A1 | 5/2020 | He |

FOREIGN PATENT DOCUMENTS

| | | |
|---|---|---|
| CN | 104640506 A | 5/2015 |
| CN | 105232085 A | 1/2016 |
| CN | 105455851 A | 4/2016 |
| CN | 105844645 A | 8/2016 |
| CN | 106037816 A | 10/2016 |
| CN | 106232013 A | 12/2016 |
| CN | 106419960 A | 2/2017 |
| CN | 106419961 A | 2/2017 |
| CN | 106618635 A | 5/2017 |
| CN | 106805997 A | 6/2017 |
| CN | 107440740 A | 12/2017 |
| CN | 107505232 A | 12/2017 |
| JP | 2007301035 A | 11/2007 |
| RU | 2627927 | 10/2015 |
| WO | WO2011004661 A1 | 1/2011 |
| WO | WO2013017105 A1 | 2/2013 |
| WO | WO2014136502 A1 | 9/2014 |
| WO | WO2016067072 A1 | 5/2016 |
| WO | WO2017107660 | 6/2017 |
| WO | WO2019015397 A1 | 1/2019 |

OTHER PUBLICATIONS

Notice of Allowance of the parallel application KR10-2020-7004555.
"Use of the radon transform for estimation of shear wave speed", The Journal of the Acoustical Society of America 132, 1982 (2012).
The first Office Action of AU application No. 2018301988.
"Use of a Simple Non-Destructive Technique for Evaluation of the Elastic and Vibration Properties of Fiber-Reinforced and 3D Fiber-Metal Laminate Composites", Fibers 2018, 6, 14.
The EESR of EPO application No. 18835631.5.
The first OA of CA application No. 3,070,622.
The first OA of JP application No. 2020-503047.
NPL: "Shear Wave Elasticity Imaging: a New Ultrasonic Technology of Medical Diagnostics", Ultrasound in Med. & Biol., vol. 24, No. 9, pp. 1419-1435; 1998.
NPL2: "Dynamics of Picosecond Laser-Generated Acoustic Waves in Solids", Proceedings 9th Symposium on Ultrasonic Electronics. Sendai 1988. Japanese Journal of Applied Physics. vol. 23 (1989) Supplement 28-1. pp. 234-236.
The Chinese First Examination Report of corresponding Chinese application No. 201710649552.9, dated Jun. 3, 2019.
The Chinese International Search Report of corresponding International application No. PCT/CN2018/088405, dated Aug. 1, 2018.
Second Office Action of the priority application No. 201710649552.9.

* cited by examiner

_US 11,719,613 B2_

METHOD AND DEVICE FOR QUANTIFYING VISCOELASTICITY OF A MEDIUM

CROSS-REFERENCE TO RELATED APPLICATIONS

This application is a continuation of International Application No. PCT/CN2018/088405, filed on May 25, 2018, which claims priority to Chinese Patent Application No. 201710649552.9, filed on Jul. 21, 2017. The disclosures of the aforementioned applications are hereby incorporated by reference in their entireties.

TECHNICAL FIELD

The present disclosure relates to the technical field of measurement, and in particular, to a method and a device for quantifying viscoelasticity of a medium.

BACKGROUND

When performing a vibration excitation on a medium, propagation characteristics of the vibration in the medium are related to the viscoelasticity of the medium. By measuring the propagation characteristics of the vibration, the viscoelasticity of the medium can be quantified.

The above principle has been applied to many technical fields at present. Taking medical testing as an example, when testing organs or tissues such as liver, thyroid, and muscle, lesions can be located by quantifying the viscoelasticity of the medium.

Therefore, how to perform efficient and accurate viscoelasticity quantification of the medium is a problem to be solved.

SUMMARY

Embodiments of the present disclosure provide a method and a device for quantifying viscoelasticity of a medium. In order to have a basic understanding of some aspects of the disclosed embodiments, a brief summary is given below. This summary is neither a general review, nor intended to determine key/important constituent elements or to describe the protection scope of these embodiments. Its sole purpose is to present some concepts in a simplified form as a prelude of the following detailed description.

According to a first aspect of the embodiments of the present disclosure, a method for quantifying viscoelasticity of a medium is provided, and the method includes:
obtaining a position-time graph of vibration propagation after the medium is subjected to a vibration excitation;
performing angle projection along each angle within a preset angle range on the position-time graph to determine a slope of the position-time graph corresponding to an angle with maximum signal energy; and
obtaining a viscoelasticity parameter of the medium according to the slope.

Based on the method, as a first optional embodiment, the performing angle projection along each angle within a preset angle range on the position-time graph to determine a slope of the position-time graph corresponding to an angle with maximum signal energy, includes:
performing integral calculation along each angle within the preset angle range on the position-time graph;
determining an angle with a maximum integral value as a slope angle of a slope line of the position-time graph; and
determining a slope of the slope line using the slope angle.

Based on the method, as a second optional embodiment, the performing angle projection along each angle within a preset angle range on the position-time graph to determine a slope of the position-time graph corresponding to an angle with maximum signal energy, includes:
calculating a gray-level co-occurrence matrix along each angle within the preset angle range for the position-time graph;
obtaining an image texture feature for each angle;
determining the angle with the maximum signal energy as a slope angle of a slope line of the position-time graph, using the image texture feature; and
determining a slope of the slope line using the slope angle.

Based on the method, the first embodiment, or the second embodiment, as a third optional embodiment, the method further includes:
filtering out reflected waves in the position-time graph before the angle projection.

Based on the third embodiment, as a fourth optional embodiment, the filtering out reflected waves in the position-time graph, includes: performing direction filtering on the position-time graph.

Based on the method, the first embodiment, or the second embodiment, as a fifth optional embodiment, the obtaining a position-time graph of vibration propagation, includes:
obtaining the position-time graph of the vibration propagation along a set vibration propagation direction.

According to a second aspect of the embodiments of the present disclosure, a device for quantifying viscoelasticity of a medium is provided, and the device includes:
an image module, configured to obtain a position-time graph of vibration propagation after the medium is subjected to a vibration excitation;
a determining module, configured to perform angle projection along each angle within a preset angle range on the position-time graph to determine a slope of the position-time graph corresponding to an angle with maximum signal energy; and
a quantifying module, configured to obtain a viscoelasticity parameter of the medium according to the slope.

Based on the device, as a first optional embodiment, the determining module includes:
a calculating sub-module, configured to perform integral calculation on the position-time graph along each angle within the preset angle range;
a determining sub-module, configured to determine an angle with a maximum integral value calculated by the calculating sub-module as a slope angle of a slope line of the position-time graph; and determine a slope of the slope line using the slope angle.

Based on the device, as a second optional embodiment, the determining module includes:
a calculating sub-module, configured to calculate a gray-level co-occurrence matrix along each angle within the preset angle range for the position-time graph;
a determining sub-module, configured to obtain an image texture feature of each angle; determine the angle with the maximum signal energy as a slope angle of a slope line of the position-time graph, using the image texture feature; and determine a slope of the slope line using the slope angle.

Based on the device, the first embodiment, or the second embodiment, as a third optional embodiment, the device further includes:
a filtering module, configured to filter out reflected waves in the position-time graph before the angle proj ection.

Based on the device, the first embodiment, or the second embodiment, as a fourth optional embodiment, the image module obtains the position-time graph of the vibration propagation along a set vibration propagation direction.

According to a third aspect of the embodiments of the present disclosure, a device for quantifying viscoelasticity of a medium is provided, and the device includes:

a memory, storing execution instructions;

a processor, configured to read the execution instructions to accomplish the following operations:

obtaining a position-time graph of vibration propagation after the medium is subjected to a vibration excitation;

performing angle projection along each angle within a preset angle range on the position-time graph to determine a slope of the position-time graph corresponding to an angle with maximum signal energy; and obtaining a viscoelasticity parameter of the medium according to the slope.

The technical solutions provided by the embodiments of the present disclosure may include the following beneficial effects:

the angle with the maximum signal energy in the position-time diagram is determined using the angle projection, the angle with the maximum signal energy corresponds to the slope of the position-time graph, and the slope of the position-time graph is the propagation velocity of the vibration in the medium. Since the propagation velocity of the vibration in the medium is related to the viscoelasticity of the medium, the viscoelasticity parameter of the medium can be quantitatively calculated after the slope of the position-time graph is obtained. The embodiments of the present disclosure do not need to select feature points from the position-time graph to calculate the slope of the position-time graph, and is not affected by noise and has a small calculation amount, and can efficiently and accurately quantifies the viscoelasticity of the medium.

It should be understood that the above general description and the following detailed description are merely exemplary and explanatory, and should not limit the present disclosure.

BRIEF DESCRIPTION OF DRAWINGS

The drawings herein are incorporated in and constitute a part of the present specification, illustrating the embodiments consistent with the present disclosure, and serving to explain the principles of the present disclosure together with the description.

DESCRIPTION OF EMBODIMENTS

The following description and the drawings sufficiently illustrate specific embodiments of the present disclosure to enable those skilled in the art to practice them. The embodiments represent only possible variations. Unless otherwise explicitly required, individual components and functions are optional, and the order of operations may be varied. Parts and features of some embodiments may be included in or replace parts and features of other embodiments. The scope of embodiments of the present disclosure includes the entire scope of the claims, and all available equivalents of the claims. Herein, the various embodiments may be individually or collectively represented by the term "invention", which is for convenience only, and if more than one invention is actually disclosed, it is not intended to automatically limit the scope of the application to any single invention or inventive concept. Herein, relational terms such as first and second are used only to distinguish one entity or operation from another entity or operation, and do not require or imply that there is any actual relationship or order between these entities or operations. Moreover, the terms "including", "containing" or any other variation thereof are intended to encompass non-exclusive inclusion, such that processes, methods, or devices that include a series of elements include not only those elements, but also other elements not explicitly listed. The various embodiments herein are described in a progressive manner, each embodiment focuses on the differences from other embodiments. For the same and similar parts between the various embodiments, reference can be made to each other. As for the structures and products or the like disclosed in the embodiments, since they correspond to the parts disclosed in the embodiments, the description is relatively simple, and reference can be made to the description of the method part for the relevant parts.

Figure 1:
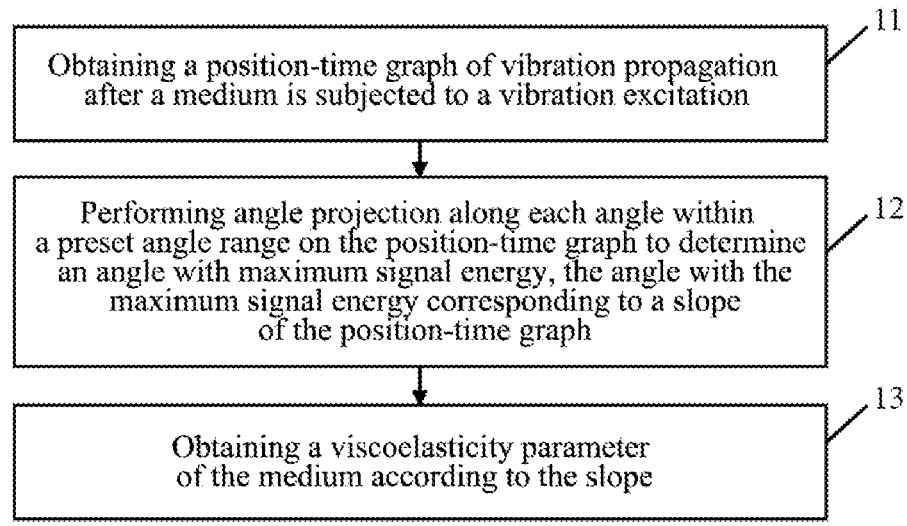
FIG. 1 shows a flow chart of a method for quantifying viscoelasticity of a medium according to an exemplary embodiment.

FIG. 1 shows a flow chart of a method for quantifying viscoelasticity of a medium according to an exemplary embodiment. As shown in FIG. 1, the method includes the following steps.

In step 11, obtaining a position-time graph of vibration propagation after the medium is subjected to a vibration excitation.

In step 12, performing angle projection along each angle within a preset angle range on the position-time graph to determine an angle with maximum signal energy, which corresponds to a slope of the position-time graph.

The preset angle range refers to an angle range for performing the angle projection selected according to actual situations. As an optional implementation, the preset angle range may be 360 degree, and accordingly a full-angled angle projection is required to be performed. As another optional implementation, the angle range for performing the angle projection is selected according to the characteristics of the obtained position-time graph. The horizontal axis of the position-time graph obtained in step 11 indicates time and the vertical axis indicates position. If the vibration propagates to a distant place only from the starting point of the vibration excitation, when the velocity of vibration propagation is infinitely large, it is close to a straight line parallel to the vertical axis on the position-time graph, and when the velocity of the vibration propagation is infinitely small, it is close to a straight line parallel to the horizontal axis on the position-time graph. At this time, a preset angle range of 90 degree can meet the needs, without the need to perform full-angle projection, and then the efficiency of quantifying the viscoelasticity of the medium is improved. If the vibration can also continue to propagate in an opposite direction besides propagating to the distant place from the starting point of the vibration excitation, the preset angle range may be 180 degree. As for the actual starting point and ending point of the preset angle range, with the rectangular coordinate system remaining unchanged, it is related to the starting point of 0 degree and the counterclockwise or clockwise rotation direction, which can be selected as needed, as long as the preset angle range is guaranteed.

Each angle refers to each angle within the preset angle range along which the angular projection is performed. The selection of specific angle is determined according to a time accuracy requirement and a calculation speed requirement. The higher the time accuracy requirement is, the higher the accuracy requirement of angle selection is; and the higher the calculation speed requirement is, the lower the accuracy requirement of angle selection is. For example, it can be selected from 0.01 degree to 1 degree.

The angle projection refers to performing image feature recognition or extraction on set angles to determine an angle with the maximum signal energy.

In step 13, obtaining a viscoelasticity parameter of the medium according to the slope.

The viscoelasticity parameter includes at least one of a viscosity parameter and an elastic parameter.

The slope of the position-time graph is determined by a distance of vibration propagation per unit time, that is, the velocity of the vibration propagation in the medium. In a homogeneous medium, the velocity of vibration propagation is related to the viscoelasticity of the medium. The viscoelasticity parameter of the medium can be quantitatively calculated after the slope of the position-time graph is obtained. Therefore, how to efficiently and accurately obtain the above slope becomes a key of quantifying the viscoelasticity of the medium. In the present exemplary embodiment, the angle with the maximum signal energy is determined using the angle projection. Since the angle with the maximum signal energy corresponds to the slope of the position-time graph, that is, it is equivalent to obtain the slope of the position-time graph. This method does not need to select a peak, a trough, or a certain phase of vibration from the position-time graph as a feature point to calculate the slope of the position-time graph. It is not affected by noise and has a small calculation amount. It is an efficient and accurate method for quantifying the viscoelasticity of the medium.

In an exemplary embodiment, after performing the vibration excitation on the medium through mechanical vibration, acoustic radiation force, or other manners capable of generating vibration, the medium generates vibration, and the vibration propagates in the medium. Due to the limited propagation velocity of the above vibration in the medium, a detection wave can be used to perform dynamic imaging for the medium. The above detection wave may be a light wave, an ultrasonic wave, or the like. The above dynamic imaging may be one-dimensional imaging, two-dimensional imaging, or three-dimensional imaging.

When the above-mentioned vibration propagates in the medium, the wave-front will reach different positions along the propagation direction at different times. The echo signal generated for the imaging of the medium by the detection wave will undergo phase decorrelation. Utilizing this characteristic of phase decorrelation, motion information of the medium can be obtained through algorithms such as cross-correlation, autocorrelation, and optical flow. The position-time graph can be obtained along the set vibration propagation direction. The above algorithms may be various methods based on block matching or non-block matching. The above set vibration propagation direction is an actual propagation direction of the vibration when the vibration propagates in only one propagation direction, and is a selected propagation direction when the vibration propagates in multiple propagation directions. For example, when the medium is a uniform sheet, after the medium is excited by vibration, the vibration will propagate along the extension direction of the sheet, and the set vibration propagation direction at this time is an actual propagation direction of the vibration. For another example, when the medium has a stereoscopic irregular shape, the wave-front of the vibration propagation has a three-dimensional shape (for example, the wave-front of the vibration propagation is an ellipsoid), then different position-time graphs are obtained along different vibration propagation directions, and the set vibration propagation direction at this time is a selected propagation direction of interest. The above-mentioned propagation direction of interest is determined according to a direction that needs to be actually measured, for example, it may be at least one of a direction in which the vibration propagates fastest, a direction in which the vibration propagates slowest, and a direction in which the velocity of the vibration propagation is within a certain range.

Figure 2:
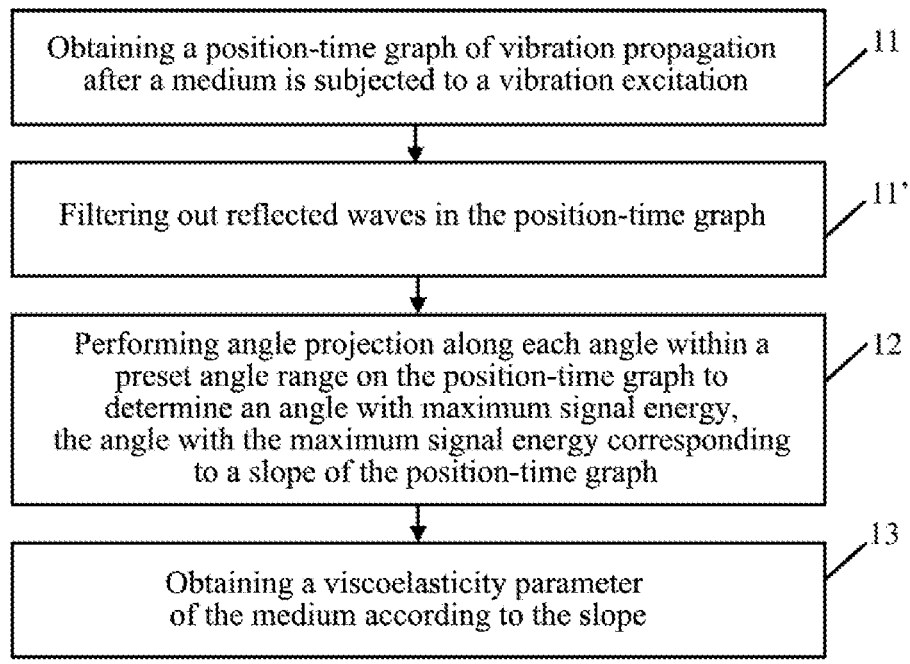
FIG. 2 shows a flow chart of a method for quantifying viscoelasticity of a medium according to an exemplary embodiment.

In an exemplary embodiment, when the vibration propagates in the medium, reflected waves are generated when the vibration encounters edges of the medium or foreign objects. To improve the accuracy of subsequent processing, as shown in FIG. 2, before performing the angle projection, the method may also include step 11', that is, filtering out the reflected waves in the position-time graph. There are many ways to filter out, and direction filtering is one implementation of them.

In an exemplary embodiment, determining the angle with the maximum signal energy through the angle projection, and then obtaining the slope of the position-time graph, can be implemented through integral calculation. For example, integral calculation is performed along each angle within the preset angle range on the position-time graph. When an integral angle is consistent with the vibration propagation direction, the energy is gathered, and the obtained integral value at this time is maximum. Therefore, the angle with the maximum integral value is determined as the slope angle of the slope line of the position-time graph. The slope of the slope line of the position-time graph can be obtained according to the obtained slope angle, combined with position and time information. The above integral calculation is also referred to as Radon transform.

In an exemplary embodiment, since an image texture feature can be obtained by calculating a gray-level co-occurrence matrix, and the image texture feature can reflect the magnitude of the signal energy, the gray-level co-occurrence matrix can be used to obtain information of the angle with the maximum signal energy. Based on the above principle, determining the angle with the maximum signal energy through the angle projection, and then obtaining the slope of the position-time graph, can be implemented by calculating the gray-level co-occurrence matrix. For example, for the position-time graph, a gray-level co-occurrence matrix is first calculated along each angle within the preset angle range. Then, the image texture feature of each angle is obtained using the gray-level co-occurrence matrix. Then, the angle with the maximum signal energy is determined as the slope angle of the slope line of the position-time graph by using the image texture feature. Finally, the slope angle is determined using the slope angle.

According to the principle of mechanics, the viscoelasticity of the medium determines the propagation velocity of the vibration therein. Therefore, the propagation velocity of the vibration in the medium can be learned by obtaining the slope of the position-time graph. And then the viscoelasticity parameter of the medium can be quantitatively obtained according to the principle of mechanics. The viscoelasticity parameter here may include shear modulus, Young's modulus, shear viscoelasticity, shear viscosity, mechanical impedance, mechanical relaxation time, anisotropy, and the like.

The application of the method for quantifying viscoelasticity of a medium in the embodiments of the present disclosure will be given in a specific application scenario.

When a non-destructive viscoelasticity testing is performed on a viscoelastic medium such as human liver, the viscoelasticity of the medium needs to be quantified. A testing apparatus includes an exciting device and an imaging device, where the exciting device performs a vibration excitation on the medium to be detected, and the imaging device utilizes ultrasound to perform imaging for the medium after the vibration excitation. When the vibration propagates in the medium, the wave-front will reach different positions along the propagation direction at different times, forming a position-time graph. The above wave-front may be one of a peak, a trough, or the same phase of vibration.

Figure 3:
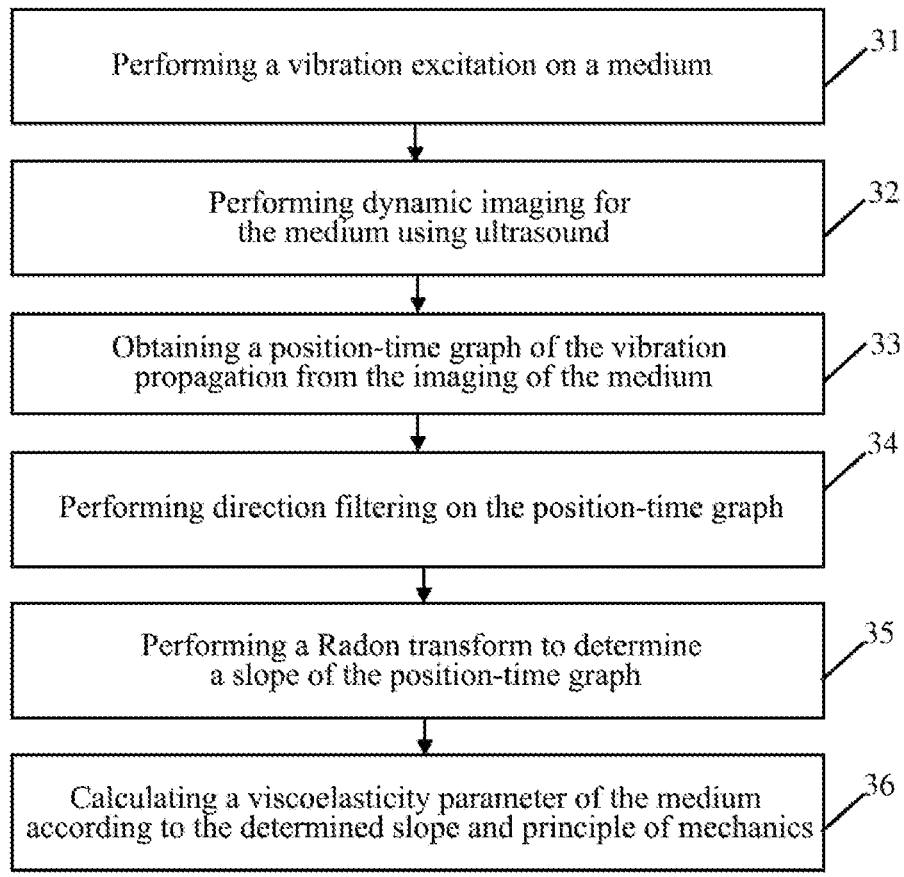
FIG. 3 shows a flow chart of a method for quantifying viscoelasticity of a medium according to an exemplary embodiment.

As shown in FIG. 3, the method for quantifying viscoelasticity of a medium in this specific application scenario may include the following steps.

In step 31, performing a vibration excitation on the medium.

In step 32, performing dynamic imaging for the medium using ultrasound.

In step 33, obtaining a position-time graph of vibration propagation from the imaging of the medium.

In step 34, performing direction filtering on the position-time graph.

In step 35, performing a Radon transform to determine a slope of the position-time graph.

In step 36, calculating a viscoelasticity parameter of the medium according to the determined slope and principle of mechanics.

In various exemplary embodiments of the above method for quantifying viscoelasticity of a medium, when there are at least two set vibration propagation directions, one position-time graph is obtained for each set vibration propagation direction correspondingly, and then the viscoelasticity parameter of the medium corresponding to the position-time graph is obtained. By synthesizing the obtained at least two sets of viscoelasticity parameters, the viscoelasticity of the medium can be evaluated more comprehensively.

The various exemplary embodiments of the method for quantifying viscoelasticity of a medium given above may be combined according to circumstances, and the combination relationship between the various exemplary embodiments is not limited here.

Figure 4:
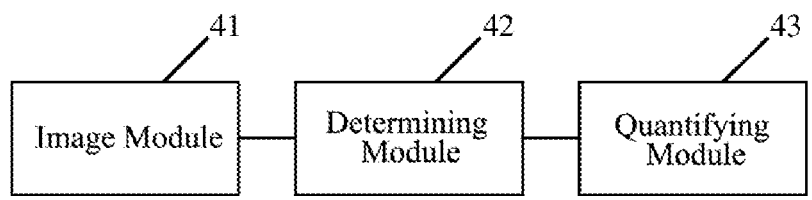
FIG. 4 shows a block diagram of a device for quantifying viscoelasticity of a medium according to an exemplary embodiment.

FIG. 4 is a block diagram of a device for quantifying viscoelasticity of a medium according to an exemplary embodiment. The device may be located in a control host of an apparatus for testing viscoelasticity of a medium, for example, in a control host of a non-destructive testing apparatus for liver in the medical testing field. The device can also be located in a cloud, and testing data of the apparatus for testing viscoelasticity of a medium needs to be processed in the cloud.

The device shown in FIG. 4 includes an image module 41, a determining module 42 and a quantifying module 43.

The image module 41 is configured to obtain a position-time graph of vibration propagation after the medium is subject to a vibration excitation.

The determining module 42 is configured to perform angle projection along each angle within a preset angle range on the position-time graph to determine an angle with maximum signal energy. The angle with the maximum signal energy described above corresponds to a slope of the position-time graph.

The quantifying module 43 is configured to obtain a viscoelasticity parameter of the medium according to the slope of the position-time graph.

Figure 5:
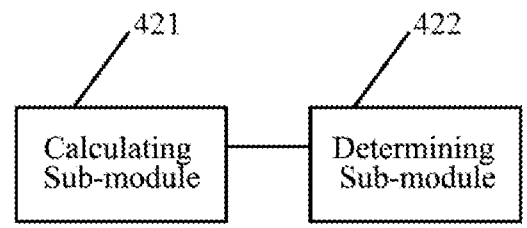
FIG. 5 is a block diagram of a determining module shown in FIG. 4.

In an exemplary embodiment, as shown in FIG. 5, the determining module 42 employs a Radon transform to perform the angle projection and determines the angle with the maximum signal energy. At this time, the determining module 42 includes a calculating sub-module 421 and a determining sub-module 422.

The calculating sub-module 421 is configured to perform integral calculation along each angle within the preset angle range on the position-time graph.

The determining sub-module 422 is configured to determine an angle with a maximum integral value calculated by the calculating sub-module 421 as a slope angle of a slope line of the position-time graph; and determine a slope of the slope line of the position-time graph through the slope angle.

As an optional implementation, when a gray-level co-occurrence matrix is used to determine the slope angle, the calculating sub-module 421 may be configured to calculate the gray-level co-occurrence matrix along each angle within the preset angle range for the position-time graph. The determining sub-module 422 may be configured to obtain an image texture feature of the each angle; determine the angle with the maximum signal energy as a slope angle of a slope line of the position-time graph using the image texture feature; and determine a slope of the slope line using the slope angle.

Figure 6:
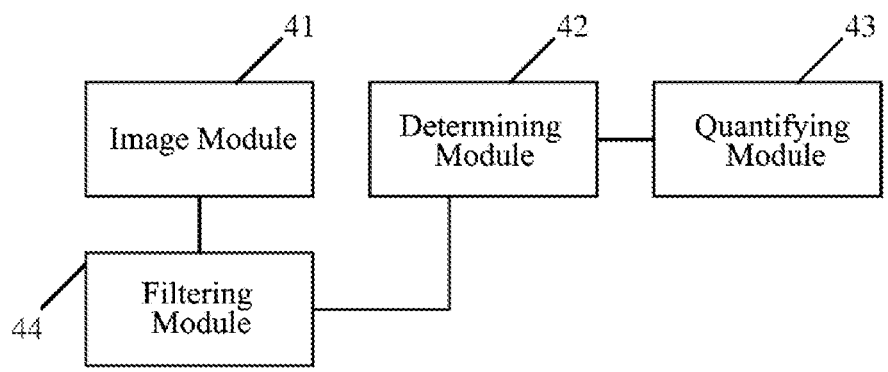
FIG. 6 shows a block diagram of a device for quantifying viscoelasticity of a medium according to an exemplary embodiment.

In an exemplary embodiment, as shown in FIG. 6, the device for quantifying viscoelasticity of a medium further includes: a filtering module 44, configured to filter out reflected waves in the position-time graph before the determination module 42 performs the angle projection.

In an exemplary embodiment, the image module 41 obtains the position-time graph of the vibration propagation along a set vibration propagation direction.

The application of the device for quantifying viscoelasticity of a medium in the embodiments of the present disclosure is given in a specific application scenario.

When performing a non-destructive viscoelasticity testing on a viscoelastic medium such as human liver, the viscoelasticity of the medium needs to be quantified. A testing apparatus includes an exciting device and an imaging device, where the exciting device performs a vibration excitation on the medium to be detected, and the imaging device utilizes ultrasound to perform imaging for the medium after the vibration excitation.

When the vibration propagates in the medium, the wave-front will reach different positions along the propagation direction at different times, forming a position-time graph. The above wave-front may be one of a peak, a trough, or the same phase of vibration. The device for quantifying viscoelasticity of a medium obtains the position-time graph of the vibration propagation from the imaging of the medium along the set propagation direction. Then the device for quantifying viscoelasticity of a medium performs integral calculation along each angle on the position-time graph, and determines the angle with the maximum integral value as the slope angle of the slope line of the position-time graph, and then determines the slope of the position-time graph. Finally, the device for quantifying viscoelasticity of a medium calculates and obtains the viscoelasticity parameter of the medium according to the determined slope and principle of mechanics.

Figure 7:
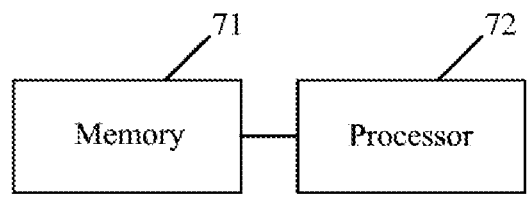
FIG. 7 shows a block diagram of a device for quantifying viscoelasticity of a medium according to an exemplary embodiment.

FIG. 7 is a block diagram of a device for quantifying viscoelasticity of a medium according to an exemplary embodiment. The device may be located in a control host of an apparatus for testing viscoelasticity of a medium, for example, in a control host of a non-destructive testing apparatus for liver in the medical testing field. The device can also be located in a cloud, and testing data of the apparatus for testing viscoelasticity of a medium needs to be processed in the cloud.

The various exemplary embodiments of the device for quantifying viscoelasticity of a medium given above may be combined according to circumstances, and the combination relationship between the various exemplary embodiments is not limited here.

The device shown in FIG. 7 includes: a memory 71 and a processor 72.

The memory 71 stores execution instructions.

The processor 72 is configured to read the execution instructions from the memory 71 to execute some or all steps in the exemplary embodiments of the method for quantifying viscoelasticity of a medium described above. The processor 72 may be implemented by a chip.

If the device for quantifying viscoelasticity of a medium shown in FIG. 7 is located in the control host of the apparatus for testing viscoelasticity of a medium, it can be connected to an exciting device and an imaging device in the apparatus for quantifying viscoelasticity of a medium by bus, wireless, etc. At this time, the device has interfaces to realize the above connections and corresponding communication mechanism.

If the device for quantifying viscoelasticity of a medium shown in FIG. 7 is located in the cloud, it can communicate with the apparatus for testing viscoelasticity of a medium through a network.

It should be understood that the present disclosure is not limited to the processes and structures that have been described above and shown in the drawings, and various modifications and changes can be made without departing from the scope thereof. The scope of the present disclosure is only limited by the appended claims.

What is claimed is:

1. A method for quantifying viscoelasticity of a medium, wherein the method comprises:
    generating, by an exciting device, a vibration excitation on the medium to make the medium generate vibration and make the vibration propagate in the medium;
    performing, by an imaging device, imaging for the medium after the vibration excitation is generated by virtue of a detection wave of the imaging device;
    obtaining, by the imaging device, a position-time graph of vibration propagation along a set vibration propagation direction from dynamic imaging of the medium, wherein a horizontal axis of the position-time graph indicates time, and a vertical axis of the position-time graph indicates a position of wave-front of the vibration;
    performing angle projection along directions having respective angles relative to a preset line of 0 degree on the position-time graph to determine a slope of the position-time graph corresponding to an angle with maximum signal energy, wherein the respective angles are within a preset angle range; and
    obtaining, according to the slope, propagation velocity of the vibration, and determining, according to principle of mechanics and the propagation velocity of the vibration, a viscoelasticity parameter of the medium;
    wherein the performing the angle projection along the directions having respective angles relative to the preset line of 0 degree on the position-time graph to determine the slope of the position-time graph corresponding to the angle with maximum signal energy, comprises:
    performing integral calculation along each angle within the preset angle range on the position-time graph, wherein the integral calculation is Radon transform;
    determining an angle corresponding to a maximum integral value obtained by the Radon transform as a slope angle of a slope line of the position-time graph; and
    determining the slope of the slope line using the slope angle.

2. The method according to claim 1, wherein the method further comprises:
    filtering out reflected waves in the position-time graph before the performing the angle projection.

3. The method according to claim 2, wherein the filtering out the reflected waves in the position-time graph, comprises:
    performing direction filtering on the position-time graph.

4. A device for quantifying viscoelasticity of a medium, wherein the device comprises:
    a memory, storing execution instructions; and
    a processor, configured to read the execution instructions to:
    generate a vibration excitation on the medium to make the medium generate vibration and make the vibration propagate in the medium;
    perform imaging for the medium after the vibration excitation is generated by virtue of a detection wave of an imaging device;
    obtain a position-time graph of vibration propagation along a set vibration propagation direction from the dynamic imaging of the medium, wherein a horizontal axis of the position-time graph indicates time, and a vertical axis of the position-time graph indicates a position of wave-front of the vibration;
    perform angle projection along directions having respective angles relative to a preset line of 0 degree on the position-time graph to determine a slope of the position-time graph corresponding to an angle with maximum signal energy, wherein the respective angles are within a preset angle range; and
    obtain, according to the slope, propagation velocity of the vibration, and determine, according to principle of mechanics and the propagation velocity of the vibration, a viscoelasticity parameter of the medium;
    wherein the processor is configured to read the execution instructions to:
    perform integral calculation along each angle within the preset angle range on the position-time graph, wherein the integral calculation is Radon transform;
    determine an angle corresponding to a maximum integral value obtained by the Radon transform as a slope angle of a slope line of the position-time graph; and
    determine the slope of the slope line using the slope angle.

5. The device according to claim 4, wherein the processor is further configured to read the execution instructions to:
    filter out reflected waves in the position-time graph before performing the angle projection.

* * * * *